(12) United States Patent
Hasegawa (10) Patent No.: US 6,929,620 B2
(45) Date of Patent: Aug. 16, 2005

(54) INJECTOR FOR LIQUID MEDICINE

(75) Inventor: Mitsuru Hasegawa, Osaka (JP)

(73) Assignee: Nipro Corporation, Osaka (JP)

( * ) Notice: Subject to any disclaimer, the term of this patent is extended or adjusted under 35 U.S.C. 154(b) by 235 days.

(21) Appl. No.: 10/097,485

(22) Filed: Mar. 15, 2002

(65) Prior Publication Data

US 2002/0138039 A1 Sep. 26, 2002

(30) Foreign Application Priority Data

| Mar. 21, 2001 | (JP) | 2001-080088 |
| Apr. 27, 2001 | (JP) | 2001-131514 |
| May 7, 2001 | (JP) | 2001-135913 |

(51) Int. Cl.$^7$ .......... A61M 37/00; A61M 5/00; A61B 19/00; A61N 5/00
(52) U.S. Cl. .......... 604/82; 604/88; 604/414; 604/247; 600/5
(58) Field of Search .......... 604/82–89, 414, 604/202, 90, 500, 181, 191, 539, 175, 533, 246, 535, 247, 411, 415, 68, 413, 537; 600/5, 321; 137/512.15, 843

(56) References Cited

U.S. PATENT DOCUMENTS

| 4,059,109 A | * | 11/1977 | Tischlinger | 604/88 |
| 4,372,294 A | * | 2/1983 | Strauss et al. | 424/1.17 |
| 4,424,057 A | * | 1/1984 | House | 604/88 |
| 5,102,388 A | * | 4/1992 | Richmond | 604/88 |

FOREIGN PATENT DOCUMENTS

| DE | 199 09 654 A | 7/2000 |
| WO | 99/21600 A | 5/1999 |

* cited by examiner

*Primary Examiner*—Nicholas D. Lucchesi
*Assistant Examiner*—Roz Maiorino
(74) *Attorney, Agent, or Firm*—Birch, Stewart, Kolasch & Birch, LLP (57) ABSTRACT

An injector for liquid medicine comprises a cylindrical body 1, first and second gasket 2, 3 contained in a lumen of cylindrical body 1. The cylindrical body 1 is provided with a fluid inlet 13 and a fluid outlet 14 in opposite sides of the cylindrical body 1 with respect to the longitudinal axis thereof. Second gasket 3 is spaced from the first gasket 2 to form a fluid chamber 4 between them. The first gasket 2 is adapted to be moved by sliding along the inner wall of the cylindrical body 1 from a first position to the distal end 11 of cylindrical body 1 via a second position. The fluid inlet 13 is opened at a position closer to the distal end 11 of the cylindrical body 1 than the outlet 14 is. The first gasket 2 is stopped at a second position where the fluid chamber 4 is communicated with the fluid outlet 14 but prevented from fluid-communication with the fluid inlet 13.

5 Claims, 13 Drawing Sheets

INJECTOR FOR LIQUID MEDICINE

BACKGROUND OF THE INVENTION

1. Field of the Invention

The present invention relates to an injector for liquid medicine and, more particularly, an injector which enables to continually administer a little dose of a liquid medicine after priming. The injector of the present invention is useful for administration of an additional medicine in midstream of administration of one medicine and for administration of a medicine which may cause infection of an operator during mixed administration of different medicines such as antitumor agents.

2. Background Art

When performing administration of a liquid medicine with an infusion set or a catheter, it is frequently necessary to administer another medicine in midstream of administration. Such operations are required, for example, in administration of contrast media, hormone preparations, peptide preparations, antitumor agents, vitamin preparations, etc. This is generally done using a prefilled syringe, i.e., a syringe with a liquid medicine previously charged therein.

So far, such mixed administration has been carried out using a three-way stopcock or a Y-shaped tube to change over route of administration.

However, use of the three-way stopcock or Y-shaped tube may cause leakage of the charged medicine at the time of connection of the prefilled syringe or priming operation. In particular, in case of medicines such as antitumor agents which are high in carcinogen, the leakage of such a medicine may causes health problems of the operator. Further, the administration of a little dose of expensive medicine is difficult to operate and makes it difficult to perform effective administration since the medicine may be diluted with other medicine. In addition, there is a problem such that the medicine is remained in route of administration.

SUMMARY OF THE INVENTION

It is therefore an object of the present invention to provide an injector for liquid medicine which is easy to operate, makes it possible to continually administer a little dose of a liquid medicine different from a first liquid medicine during administration of the first liquid medicine.

According to one aspect of the present invention, there is provided an injector for liquid medicine comprising:

a cylindrical body having an opening at each end thereof and provided with a fluid inlet and a fluid outlet in opposite sides of the cylindrical body with respect to the longitudinal axis thereof, said inlet and outlet being respectively communicated with a lumen of the cylindrical body, said inlet being located at a position closer to the distal end of the cylindrical body than the fluid outlet is; and first and second gaskets fluid-tightly and slidably arranged in the lumen of said cylindrical body and adapted to be moved along an inner wall of said cylindrical body, said first and second gaskets being spaced from one another to form a fluid chamber between them, said fluid chamber being filled with a liquid medicine;

said first gasket being slidable from a first position where the fluid inlet and outlet are communicated with one another, to a distal end of the cylindrical body via a second position where said fluid chamber is prevented from fluid-communication with the fluid inlet but communicated with the fluid outlet to inject the liquid medicine in the fluid chamber through the fluid outlet.

The first gasket has sealing portions adjacent to each end thereof and is provided with a flow path in a central portion thereof. The fluid inlet and outlet are communicated with one another through the flow path at the first position. The cylindrical body may be provided with means for stopping the sliding movement of the first gasket at the second position. In this case, the second gasket may have sealing portions on each end thereof and is provided with a flow path between the sealing portions to allow the user to inject the medicine through the fluid inlet after administration of the medicine contained in the fluid chamber. In that case, the second gasket should allow the fluid inlet of the cylindrical body to be communicated with the fluid outlet through the flow path thereof when the first gasket is moved to the distal end of cylindrical body along with the second gasket. The flow path may be in the form of a circumferential groove or channel formed between sealing portions or in the form of a through-hole passing through the gasket.

The cylindrical body may be provided at a proximal end thereof with a plunger for pushing the second gasket toward the distal end of the cylindrical body. The stop means may be plural ribs extending from the position adapted to be engaged with the first gasket to the distal end of the cylindrical body along the inner wall of the cylindrical body.

In a preferred embodiment of the present invention, the first gasket has sealing portions adjacent to each end thereof and a flow path formed between the sealing portions. The first gasket is adapted to be moved from a first position where it allows the fluid inlet of the cylindrical body to be communicated with the fluid outlet through the flow path. At least one of the proximal end of first gasket and the distal end of the second gasket may be provided with a cylindrical protrusion having an outer diameter smaller than an inner diameter of the cylindrical body and being protruded into the fluid chamber, so that the first gasket and/or second gasket allows the fluid inlet to be communicated with the fluid outlet through an annular gap formed between the cylindrical body and the protrusion when the first gasket is moved to the distal end of cylindrical body. The flow path may be in the form of a circumferential groove or channel formed between sealing portions or in the form of a through-hole passing through the gasket perpendicular to the gasket. The cylindrical body may be provided at a proximal end thereof with a plunger for pushing the second gasket toward the distal end of the cylindrical body.

In another embodiment of the present invention, the injector further includes a third gasket located between the first and second gaskets. The third gasket is brought into contact with the proximal end of the first gasket but spaced from the second gasket to form a fluid chamber between them. At least one of the proximal end of first gasket and the distal end of the third gasket is provided with a cylindrical protrusion having an outer diameter smaller than an inner diameter of the cylindrical body and being protruded into the fluid chamber. Similarly, at least one of the proximal end of third gasket and the distal end of the second gasket is provided with a cylindrical protrusion having an outer diameter smaller than an inner diameter of the cylindrical body and being protruded into the fluid chamber.

When the first gasket is present in the first position, the first and third gaskets allow the fluid inlet to be fluid-communicated with the fluid outlet through the annular gap formed between the protrusions thereof and the inner wall of the cylindrical body. When the first gasket is moved to the distal end of the cylindrical body, the second gasket is in contact with the third gasket and the second and third gaskets allow the fluid inlet to be communicated with the fluid outlet through the annular gap formed between the protrusions thereof and the inner wall of the cylindrical body.

The injector of the present invention can be used in combination with a syringe for injection of contrast media for myocardial scintigraphy into a vein, or for infusion of hormone preparation into a dialysis circuit for treatment of renal anemia, or for administration of peptide preparations for treatment of osteoporosis, or administration of antitumor agents, or the like. Further, the injector of the present invention can be used, in combination with infusion solution bag or bottle connected thereto with tubing, for administration of vitamin preparation just before infusion of a high-calorie infusion solution to prevent Maillard reaction.

The present invention will become more fully understood from the detailed description given hereinbelow and the accompanying drawings which are given by way of illustration only, and thus are not limitative of the present invention.

DETAILED DESCRIPTION OF THE INVENTION

Figure 1:
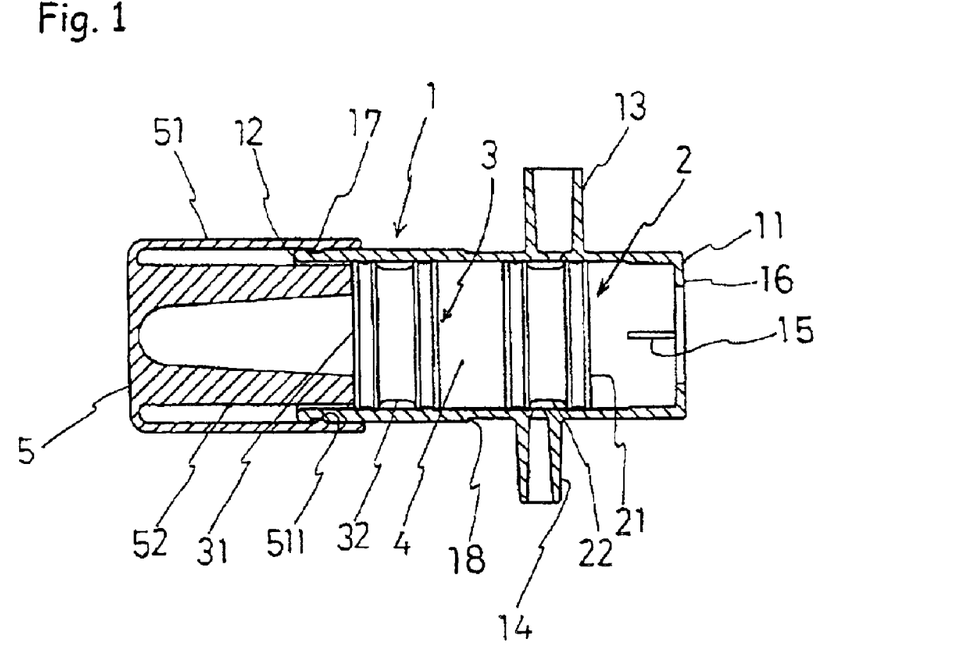
FIG. 1 is a longitudinal section illustrating an embodiment of an injector of the present invention.
Figure 6:
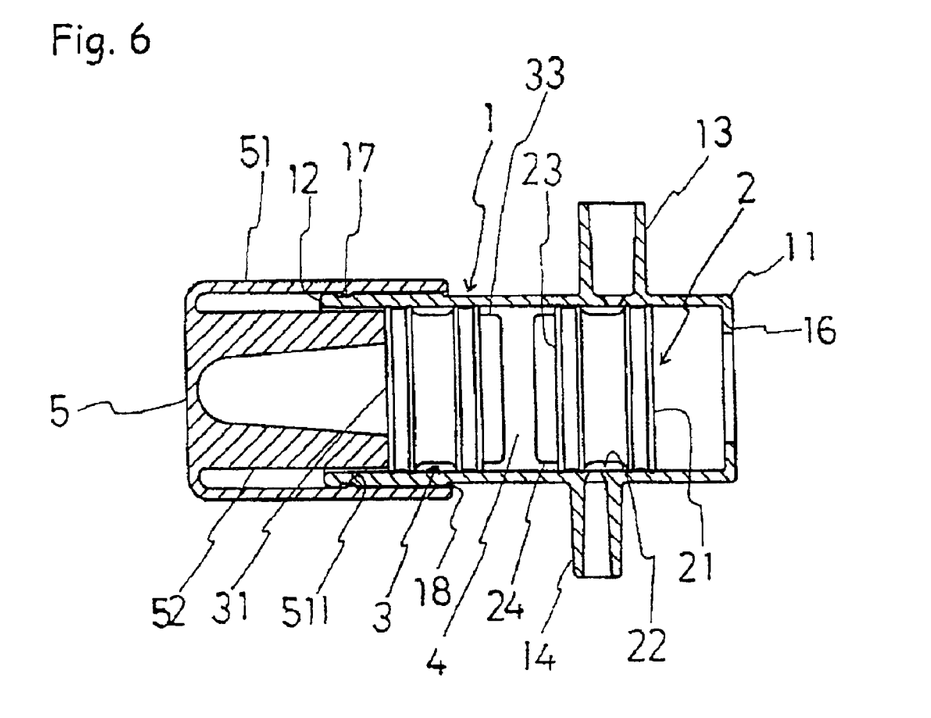
FIG. 6 is a longitudinal section illustrating another embodiment of an injector of the present invention.
Figure 10:
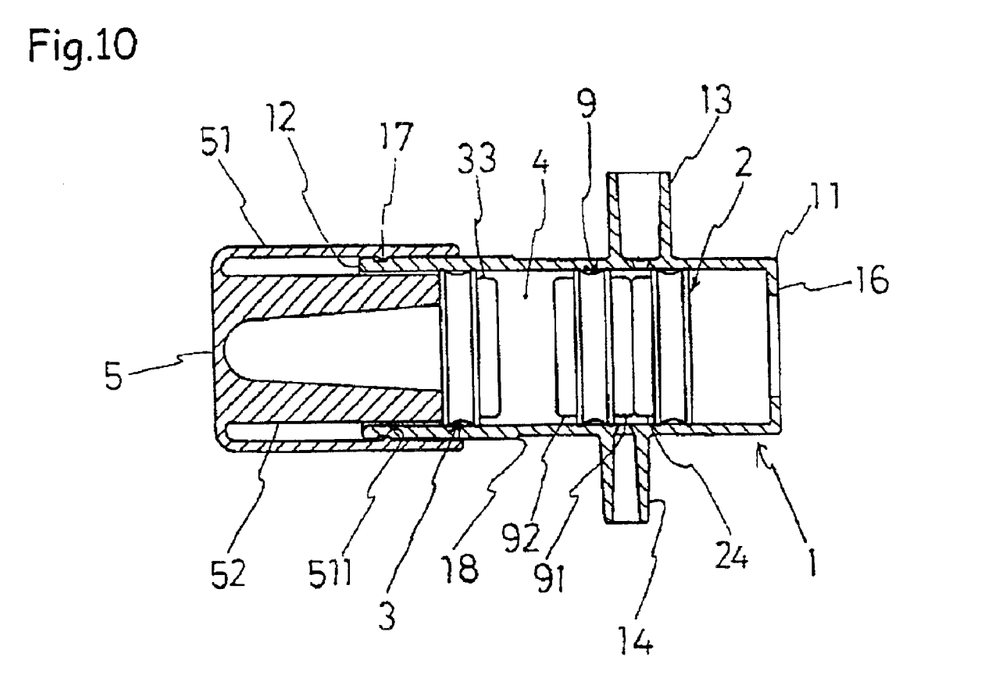
FIG. 10 is a longitudinal section illustrating another embodiment of an injector of the present invention.

As illustrated in FIGS. 1, 6 and 10, an injector of the present invention generally comprises a cylindrical body 1, a first gasket 2 contained in a lumen of the cylindrical body 1 and arranged on the side of the distal end thereof, and a second gasket 3 contained in the lumen of the cylindrical body 1 and arranged on the side of the proximal end thereof. The cylindrical body 1 is provided with a fluid inlet 13 and a fluid outlet 14 in opposite sides of the cylindrical body 1 with respect to the longitudinal axis thereof. The second gasket 3 is spaced from the first gasket 2 to form a fluid chamber 4 between them, which is filled with a liquid medicine. The first gasket 2 is adapted to be moved by sliding along the inner wall of the cylindrical body 1 from a first position to a distal end of the cylindrical body 1 via a second position. At the first position, the first gasket 2 allows the fluid inlet 13 to be fluid-communicated with the fluid outlet 14 through the flow path 22 provided in the first gasket 2. At the second position, the first gasket 2 allows the fluid chamber 4 to be prevented from fluid-communication with the fluid inlet 13 but to be fluid-communicated with the fluid outlet 14. The fluid inlet 13 is open to the lumen of the cylindrical body 1 at a position closer to the distal end 11 of the cylindrical body 1 than the fluid outlet 14 is. When the first gasket 2 is moved to the second position where the fluid chamber 4 is communicated with the fluid outlet 14 but prevented from fluid-communication with the fluid inlet 13, the liquid medicine in the fluid chamber 4 is discharged through the fluid outlet 14.

Referring now to FIG. 1, the liquid medicine injector of the first embodiment of the present invention comprises the cylindrical body 1 and the first and second gaskets 2, 3 arranged therein. The cylindrical body 1 is provided with the fluid inlet 13 and the fluid outlet 14 in opposite sides of the cylindrical body 1 with respect to the longitudinal axis thereof. The second gasket 3 is spaced from the first gasket 2 to form the fluid chamber 4 between them. The first gasket 2 is provided with the flow path 22 in a central part thereof and is movable from the first position where the flow path 22 allows the fluid inlet 13 to be communicated with the fluid outlet 14, to the distal end 11 of the cylindrical body 1. The fluid inlet 13 is open to the lumen of the cylindrical body 1 at a position closer to the distal end 11 of the cylindrical body 11 than the fluid outlet 14 is. The first gasket 2 is adapted to be stopped at the second position where the fluid chamber 4 is communicated with the fluid outlet 14 and but not fluid-communicated with the fluid inlet 13.

The cylindrical body 1 is opened at both ends 11 and 12 and provided with the fluid inlet 13 and the fluid outlet 14 in opposite sides of the cylindrical body 1 with respect to the longitudinal axis thereof. The fluid inlet 13 is open to the lumen of the cylindrical body 1 at a position which is closer to the distal end of the cylindrical body 1 than the fluid outlet 14 is. Two gaskets 2 and 3 are liquid-tightly arranged in the lumen of the cylindrical body 1 and are slidable along the lumen of the cylindrical body 1. A space formed between the first and second gaskets 2 and 3 serves as a fluid chamber 4, which is filled with a liquid medicine.

The first gasket 2 on the side of the distal end 11 of the cylindrical body 1 has sealing portions 21 adjacent to the end surfaces thereof and is provided with a flow path 22 at the central portion thereof. The flow path 22 may be in the form of a circumferential groove or channel 22 formed between sealing portions 21 or in the form of a through-hole (not shown) which crosses the first gasket 2. The first gasket 2 is movable from the first position where the fluid inlet 13 of the cylindrical body 1 is communicated with outlet 14 through the flow path 22, to the distal end 11 of cylindrical body 1. At the distal end 11 of the cylindrical body 1 there is provided an annular projection 16 inwardly extending from the distal end 11 to prevent the first gasket 2 from being moved beyond the distal end 11. The first gasket 2, when being moved toward the distal end 11 of the cylindrical body 1, is adapted to be stopped at the second position where the fluid chamber 4 is communicated with the fluid outlet 14 and but prevented from fluid-communication with the fluid inlet 13. To this end, the cylindrical body 1 is provided at the distal end thereof with means for stopping the first gasket 2. The stop means may be one or more longitudinal ribs 15 provided on the interior of the cylindrical body 1 and extending from the position being adapted to be engaged with the first gasket 2 to the distal end 11, as shown in FIG. 1. Alternatively, the stop means may be a stop member (not shown) removably fitted in the lumen of the cylindrical body 1 through the opening of the cylindrical body 1. For example, the stop member may be a cap-like member having a structure similar to that of a plunger 5 mentioned below and having a fitting portion with an outer diameter smaller than that of the annular projection 16.

The second gasket 3 on the side of the proximal end 12 may be a gasket with no flow path. Preferably, the second gasket 3 is a gasket having sealing portions 31 at both ends thereof and is provided with a flow path 32 at a central portion thereof to allow the user to inject a liquid medicine through the fluid inlet 13 after injection of the liquid medicine contained in the fluid chamber 4. In this case, it is necessary to allow the fluid inlet 13 to be communicated with the fluid outlet 14 through the flow path 32 of the second gasket 3 when the first gasket 2 is moved to the distal end 11 of the cylindrical body 1 under the condition that the first gasket 2 is brought into contact with the second gasket 3.

The cylindrical body 1 may be provided at the proximal end thereof with a plunger 5 for pushing the second gasket 3 toward the distal end 11. The plunger 5 may be a cap-like member as illustrated in FIG. 1. In this embodiment, the plunger 5 comprises a cylindrical engaging portion 51 slidably fitted on the outer wall of the cylindrical body 1 and a cylindrical protrusion 52 adapted to come into contact with the second gasket 3. The plunger 5 is adapted to be moved from a position where an annular rib 511 of the engaging portion 51 engages with an annular groove 17 of the cylindrical body 1, to a position where an annular rib 511 of the engaging portion 51 engages with a stepped portion 18 of the cylindrical body 1.

Use of the medicine injector shown in FIG. 1 will be explained below with reference to FIGS. 2 to 5 which illustrate a sequence of operation for injecting contrast media into a vein.

Figure 2:
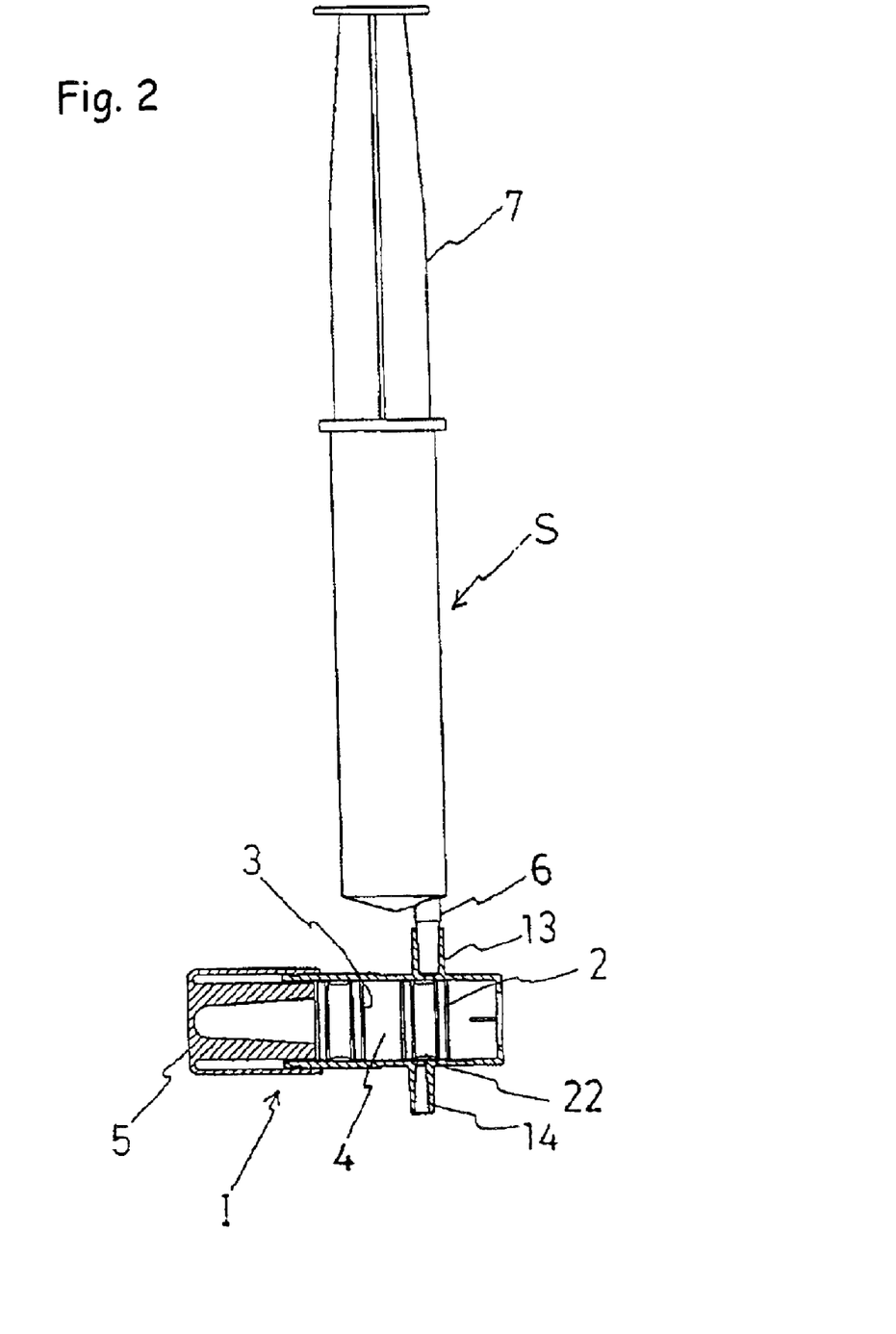
FIGS. 2 through 5 illustrate sequential steps of operation of the injector shown in FIG. 1.
Figure 3:
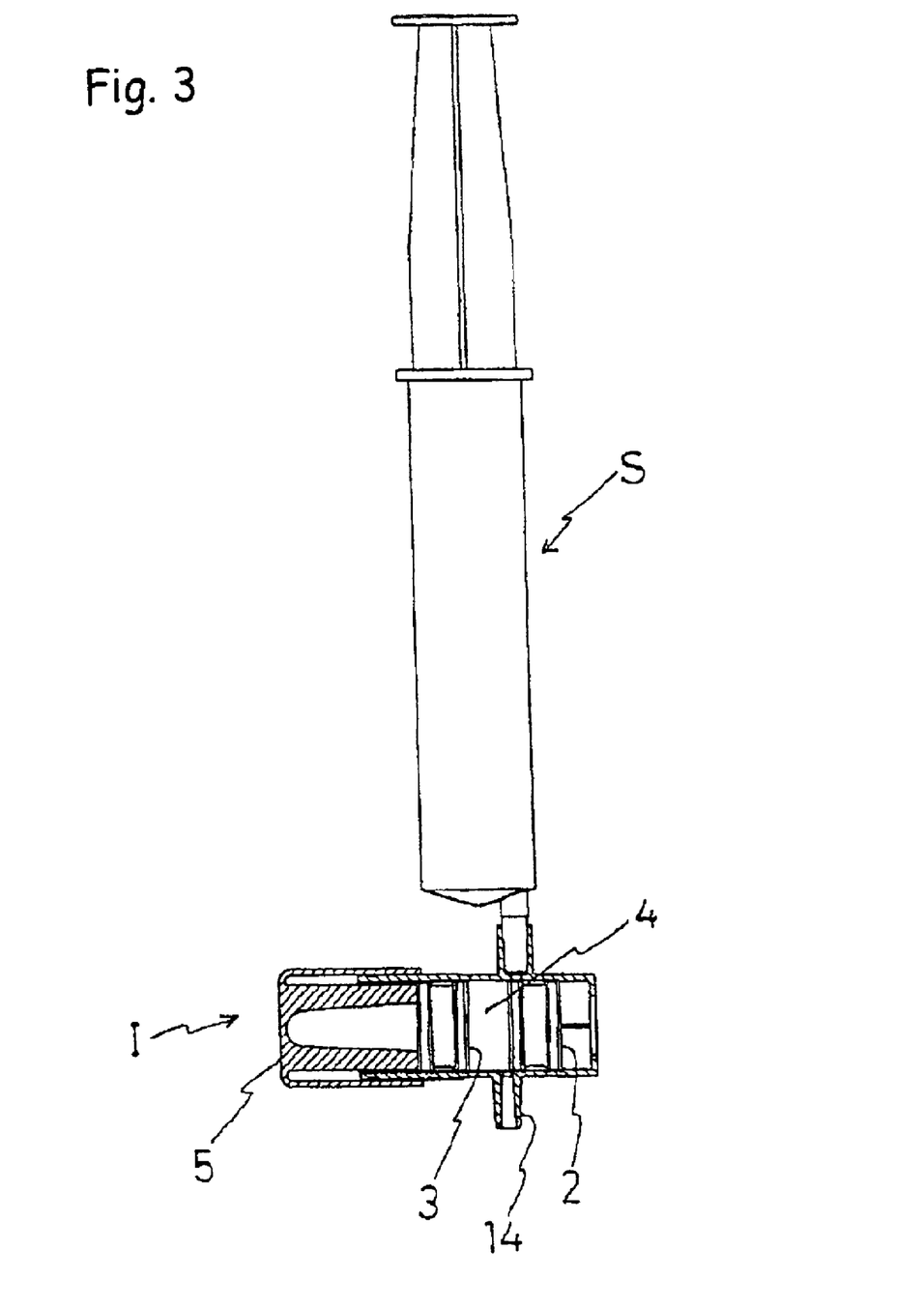

There is prepared a liquid medicine injector I with a fluid chamber 4 filled with a dose of contrast media (not illustrated). A needle, e.g., a winged catheter, is connected to the fluid outlet 14 of the injector I. At that time, the first gasket 2 is located at a first position where the flow path 22 allows the fluid inlet 13 to be communicated with the fluid outlet 14. Then, the fluid inlet 13 of the injector I is fitted with a tip 6 of a syringe S filled with a physiologic saline (not shown, herein after referred to as "saline"), as illustrated in FIG. 2. By pressing a plunger 7 of the syringe S, the saline in the syringe S is ejected forcefully through the winged catheter via the fluid inlet 13, flow path 22 and fluid outlet 14, so that the flow channel for the contrast media is washed with the saline. This operation is called as "priming".

Figure 4:
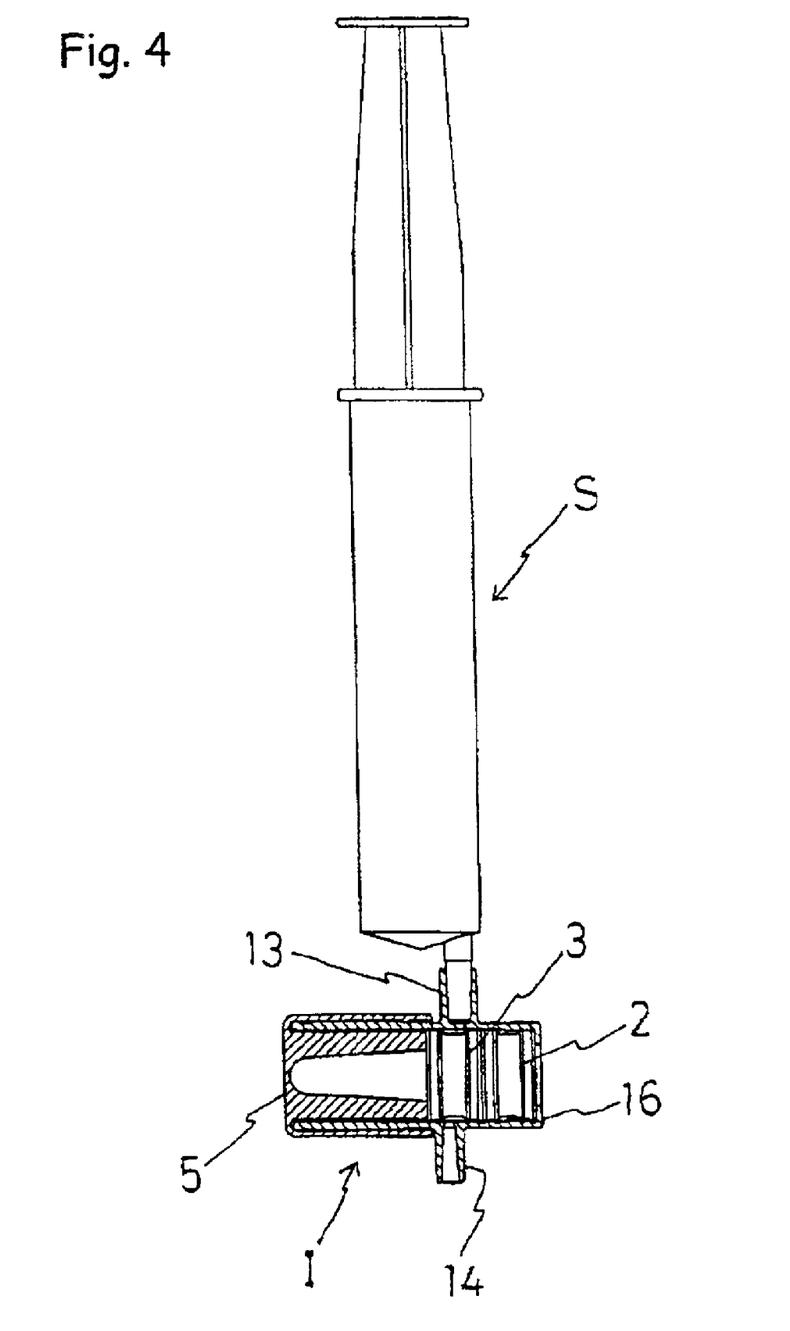
Figure 5:
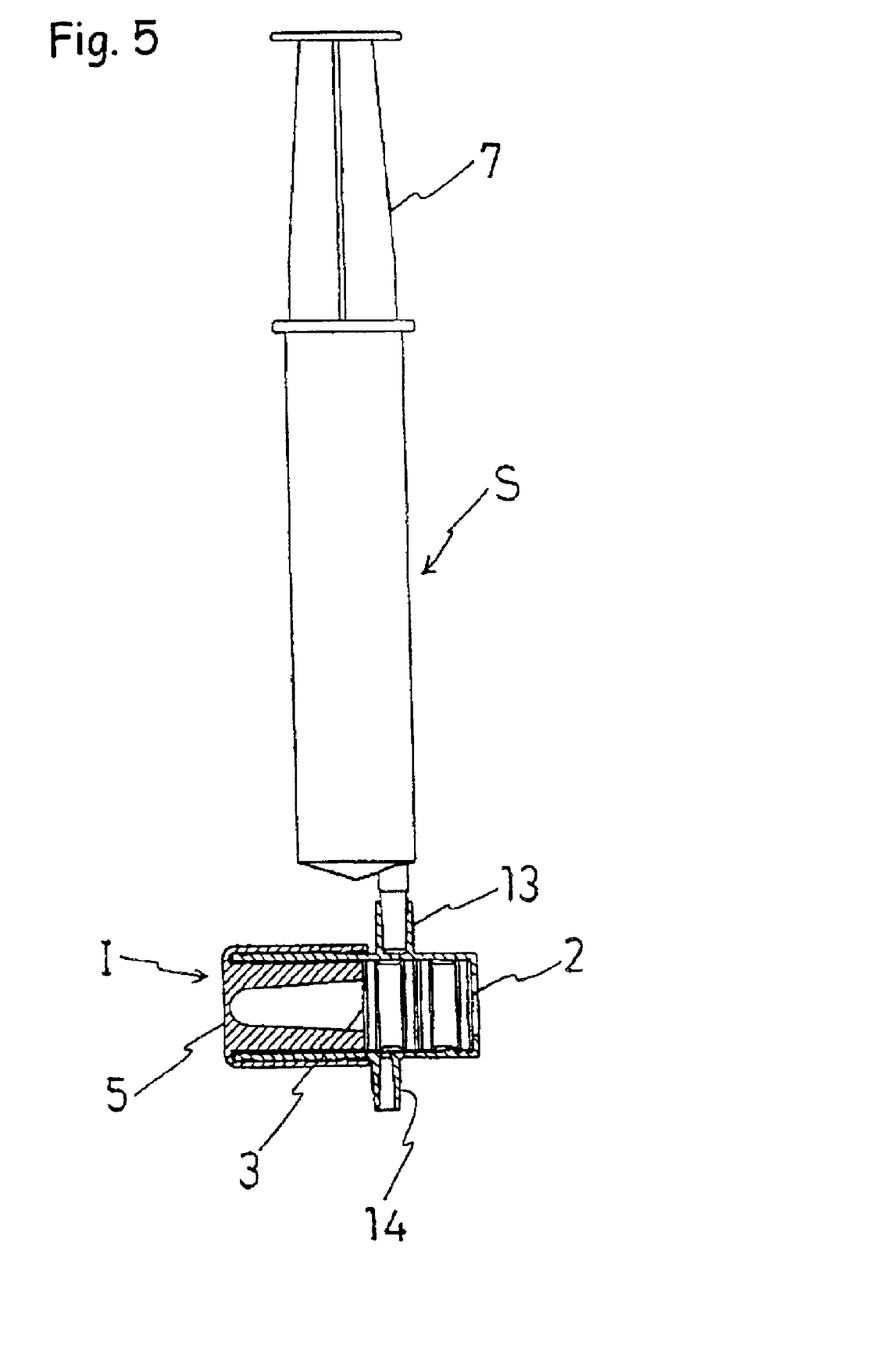

After priming, the winged catheter is inserted in a vein of a patient. The plunger 5 of the injector I is then pressed to move the second gasket 3, fluid chamber 4 and first gasket 2 toward the distal end of the injector I and stopped at a second position where the fluid chamber 4 is communicated with the fluid outlet 14 but prevented from the fluid-communication with the fluid inlet 13. By further pressing the plunger 5, the contrast media in the fluid chamber 4 is injected through the winged catheter into the vein via the fluid outlet 14 (see FIG. 3). When the fluid chamber 4 is emptied, the first and second gaskets 2 and 3 are brought into contact with one another and then moved together toward the distal end of the cylindrical body 1 until the first gasket 2 is engaged with the annular projection 16. At that time, the fluid inlet 13 is communicated with the fluid outlet 14 through the flow path 32 of the second gasket 3, as illustrated in FIG. 4. By pressing the plunger 7 of the syringe S, the saline passes through the fluid inlet 13, flow path 22, fluid outlet 14 and winged catheter so that the contrast medium remained in the fluid outlet 14 and the winged catheter is injected into the vein (cf. FIG. 5).

Referring now to FIG. 6, there is shown another embodiment of the liquid medicine injector which comprises a cylindrical body 1 and first and second gaskets 2, 3 which are fluid-tightly and movably fitted into the cylindrical body 1 and spaced from one another to form a fluid chamber 4 between them.

The first and second gaskets 2, 3 are fluid-tightly and movably fitted into the cylindrical body 1 and spaced from one another to form a fluid chamber 4 between them.

The cylindrical body 1 is opened at both ends thereof and provided in opposite faces thereof with a fluid inlet 13 and a fluid outlet 14 each having an opening communicated with an interior of the cylindrical body 1 and an axis perpendicular to the longitudinal axis of the cylindrical body 1. The fluid inlet 13 is open to the lumen of the cylindrical body 1 at a position closer to the distal end of the cylindrical body 1 than the fluid outlet 14 is. The first gasket 2 has a flow path 22 formed between the sealing portions 21, 23 and being movable from a first position where the fluid inlet 13 and outlet 14 are fluid-communicated through the flow path 22 to the distal end 11 of the cylindrical body 1. To the proximal end of the first gasket 2 and the distal end of the second gasket 3, there are provided respectively with a cylindrical protrusion 24, 33 having an outer diameter smaller than an inner diameter of the cylindrical body 1. The fluid inlet 13 is open to the lumen of the cylindrical body 1 at a position closer to the distal end 11 of the cylindrical body 1 than the fluid outlet 14 is. When the first gasket is moved to the distal end 11 of the cylindrical body 1, the fluid inlet 13 and outlet 14 are communicated with one another through the gaps between the inner wall of the cylindrical body 1 and the cylindrical protrusion 24, 33. The cylindrical body 1 is further provided with an annular projection 16 at the distal end thereof to prevent the first gasket 13 from being moved beyond the distal end 11.

The first gasket 2, which is located on the distal side of the cylindrical body 1, is a disk-shaped member having sealing portions 21, 23 adjacent to each end thereof and a flow path 22 formed between the sealing portions 21, 23. In this embodiment, the flow path 22 is an annular groove or channel formed in the circumference of the first gasket 2, but it may be a linear hole (not shown) passing through the first gasket 2. The first gasket 2 is provided on the proximal end thereof with a cylindrical protrusion 24 having an outer diameter smaller than an inner diameter of the cylindrical body 1.

The first gasket 2 is adapted to be moved from a first position where it allows the fluid inlet 13 to be communicated with the fluid outlet 14 through the flow path 22, to the distal end 11 of cylindrical body 1 via a second position where the fluid chamber 4 is communicated with the fluid outlet 14 and but prevented from the fluid-communication with the fluid inlet 13. The first gasket 2 is automatically stopped at the second position.

The second gasket 3, which is located on the proximal side of the cylindrical body 1, has a configuration similar to that of the first gasket 2 and has a cylindrical protrusion 34 having an outer diameter smaller than an inner diameter of the cylindrical body 1. In this embodiment, the cylindrical protrusions 24, 33 are provided on both the first and second gaskets, but may be provided on either first gasket 2 or second gasket 3. Thus, one of the first and second gaskets is provided with a cylindrical protrusion 24 or 33, the other gasket may be a gasket with a conventional configuration.

In order to facilitate the operation of the injector, the cylindrical body 1 may be provided at its proximal end with a plunger 5 for pushing the second gasket 3 toward the distal end 11. It is preferred to use a plunger 5 in the form of a cap-like member as illustrated in FIG. 6. The plunger 5 has a cylindrical engaging portion 51 fitted on the outer wall of the cylindrical body 1 and a cylindrical protrusion 52 which comes into contact with the second gasket 3. The plunger 5 is movable from a first position where an annular rib 511 of the engaging portion 51 engages with an annular groove 17 of the cylindrical body 1, to a second position where an annular rib 511 of the engaging portion 51 engages with a stepped portion 18 of the cylindrical body 1.

Figure 7:
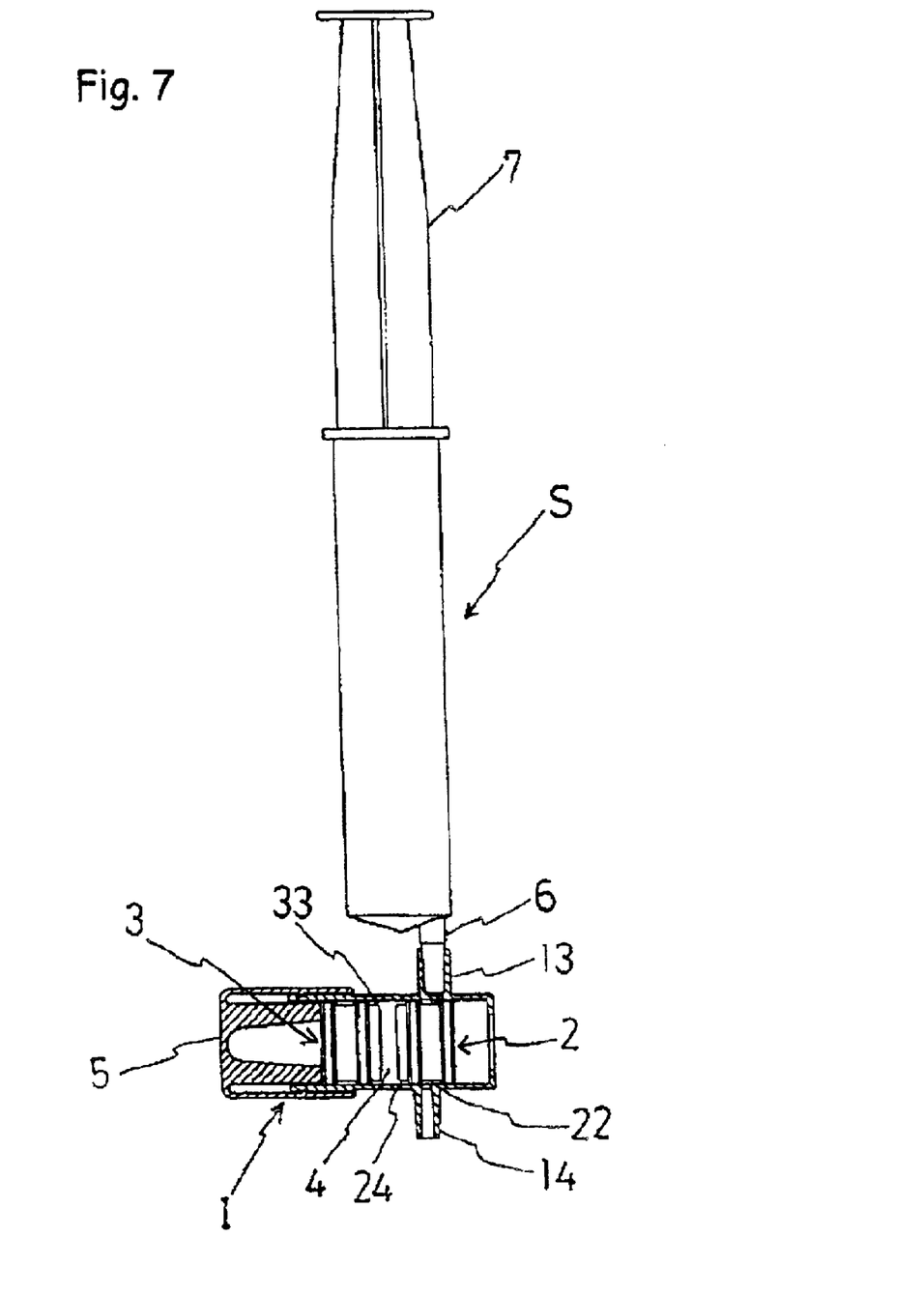
FIGS. 7 through 9 illustrate sequential steps of operation of the injector shown in FIG. 6.
Figure 8:
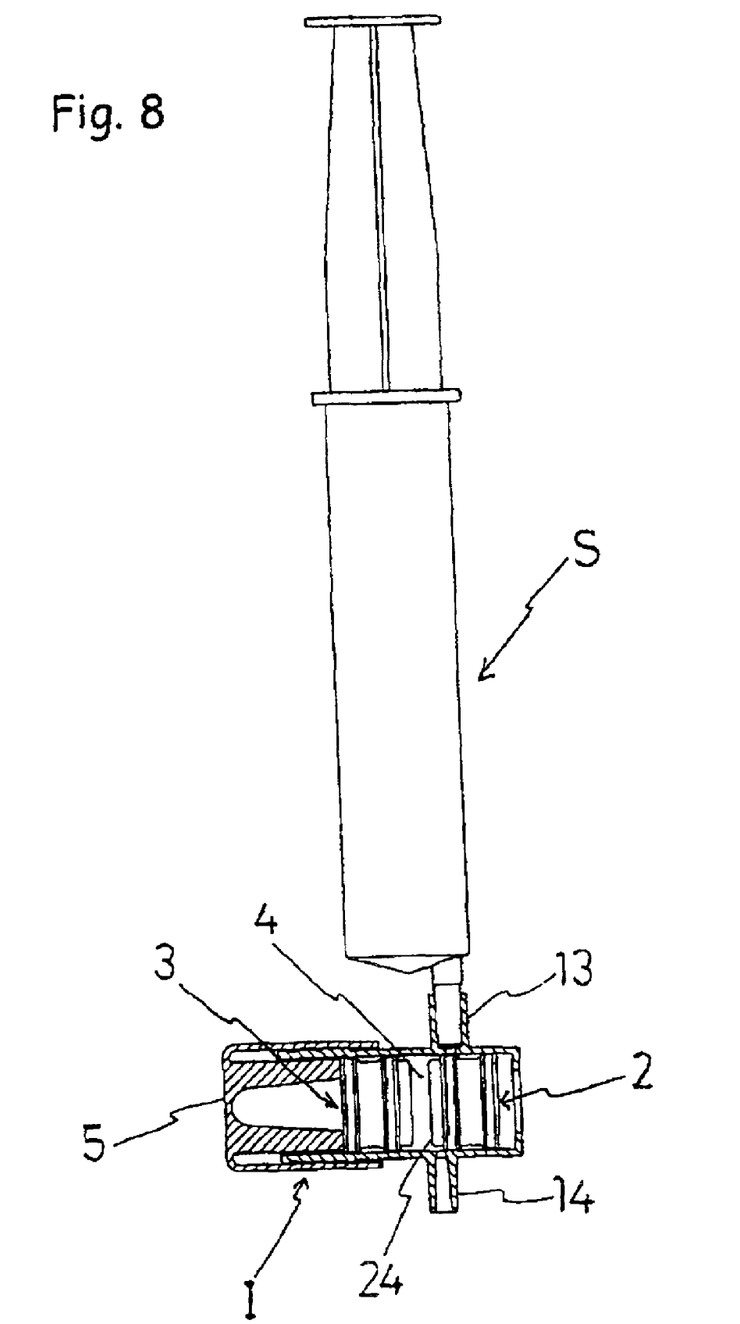
Figure 9:
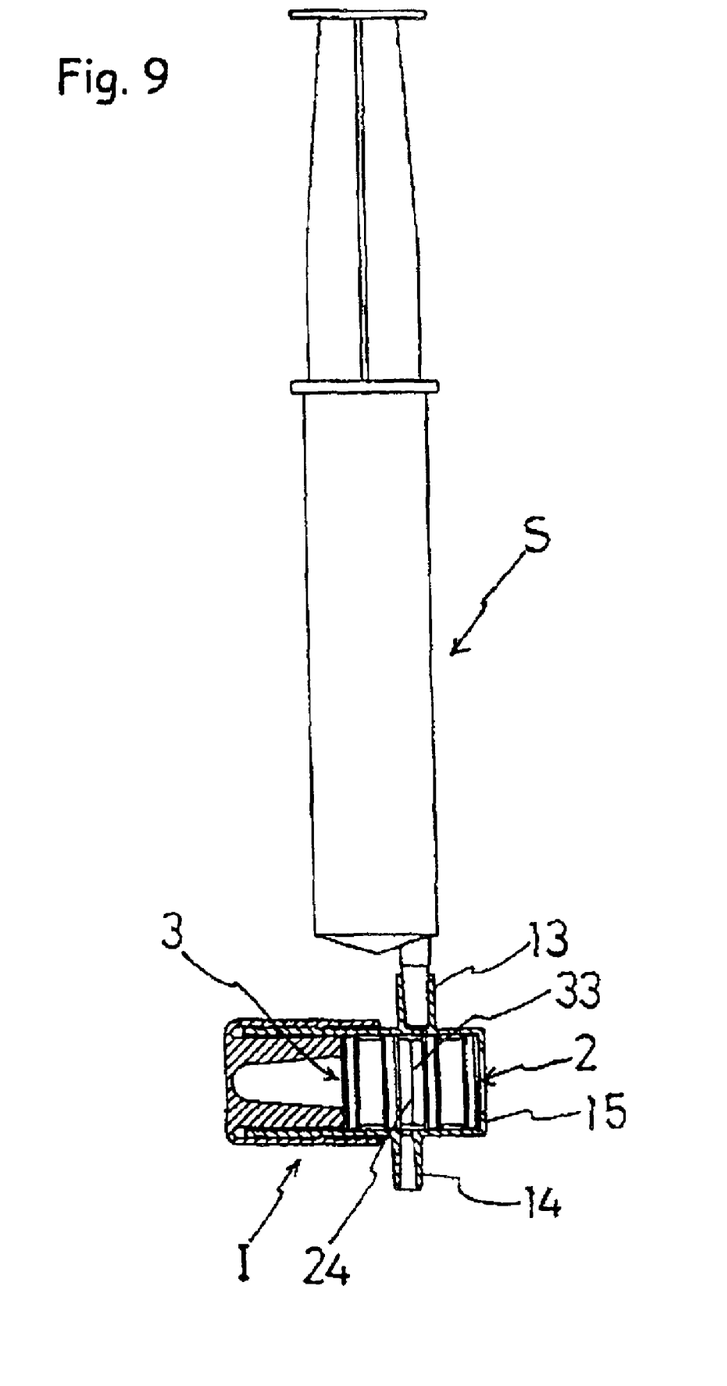

An example of how the medicine injector of FIG. 6 is used will be made with reference to FIGS. 7 to 9 which illustrate a sequence of operation for injecting contrast media into a vein.

Firstly, a needle, e.g., a winged catheter, is connected to the fluid outlet 14 of a liquid medicine injector I with a fluid chamber 4 filled with a dose of contrast media (not illustrated). At that time, the first gasket 2 is located at the first position where it allows the fluid inlet 13 to be communicated with the fluid outlet 14 through the flow path 22. Then, the injector I is fitted with a syringe S containing saline, by fitting a tip 6 of the syringe S in the fluid inlet 13 of the injector I, as illustrated in FIG. 2. By pressing a plunger 7 of the syringe S, the saline in the syringe S is ejected forcefully through the winged catheter via the fluid inlet 13, flow path 22 and fluid outlet 14, so that the whole length of the flow channel for the contrast media is washed with the saline.

After completing the above priming, the winged catheter is inserted in a vein of a patient. The plunger 5 of the injector I is then pressed to move the second gasket 3, fluid chamber 4 and first gasket 2 toward the distal end of the injector I until the first gasket 2 is stopped at the second position where the fluid chamber 4 is communicated with the fluid outlet 14 through a gap between the protrusion 24 and inner surface of the cylindrical body 1 but prevented from the fluid-communication with the fluid inlet 13, as illustrated in FIG. 8. Thus, the contrast media in the fluid chamber 4 is injected through the winged catheter into the vein by further pressing the plunger 5. As soon as the fluid chamber 4 is emptied, the second gasket 3 is brought into contact with the first gasket 2 and then moved together toward the distal end 11 of the cylindrical body 1 until the first gasket 2 reaches to the distal end 11 of the cylindrical body 1. At that time, the fluid inlet 13 is communicated with the fluid outlet 14 through the gap between the cylindrical protrusion 24, 33 and the inner wall of the cylindrical body 1, as illustrated in FIG. 9. By pressing the plunger 7 of the syringe S, the saline is injected into the vein through the fluid inlet 13, gap between the protrusion 24 and inner wall of the cylindrical body 1, fluid outlet 14 and winged catheter. Thus, the contrast media present in the gap, the fluid outlet 14 and winged catheter is injected into the vein together with the saline.

The liquid medicine injector shown in FIG. 10 comprises a cylindrical body 1 and first, second and third gaskets 2, 3 and 9 which are fluid-tightly and movably fitted into cylindrical body 1. The third gasket 9 located between the first and second gaskets 2 and 3 is brought into contact with the first gasket 2 but spaced from the second gasket 3 to form a fluid chamber 4 between the second gasket 2 and the third gasket 9. The first and second gaskets 2, 3 have the same configurations as those of embodiment of FIG. 6, while the third gasket 9 is provided at each circular end with a cylindrical protrusion 91, 92 having a diameter smaller than the inner diameter of the cylindrical body 1. Preferably, the diameter of cylindrical protrusion 91, 92 is approximately equal to that of the cylindrical protrusions 24 and 33 of the first and second gaskets 2 and 3.

The first gasket 2 is adapted to be moved together with the third gasket 9 from a first position to the distal end 11 of cylindrical body 1 via a second position. At the first position, the first and third gaskets 2 and 9 allow the fluid inlet 13 to be communicated with the fluid outlet 14 through the annular gaps formed between their protrusions 24, 91 and the inner wall of the cylindrical body 1. At the second position, the third gasket 9 allows the fluid chamber 4 to be prevented from the fluid-communication with the fluid inlet 13 but communicated with the fluid outlet 14 through the annular gaps formed between the protrusion 91 and the inner wall of the cylindrical body 1.

The cylindrical body 1 is opened at both ends 11, 12 thereof and provided in opposite faces thereof with a fluid inlet 13 and a fluid outlet 14 each having an opening communicated with a lumen of the cylindrical body 1 and an axis perpendicular to the longitudinal axis of the cylindrical body 1. Since the remaining parts of the injector are the same as that of the injector shown in FIG. 6, there would be no need to provide detailed description thereof.

Figure 11:
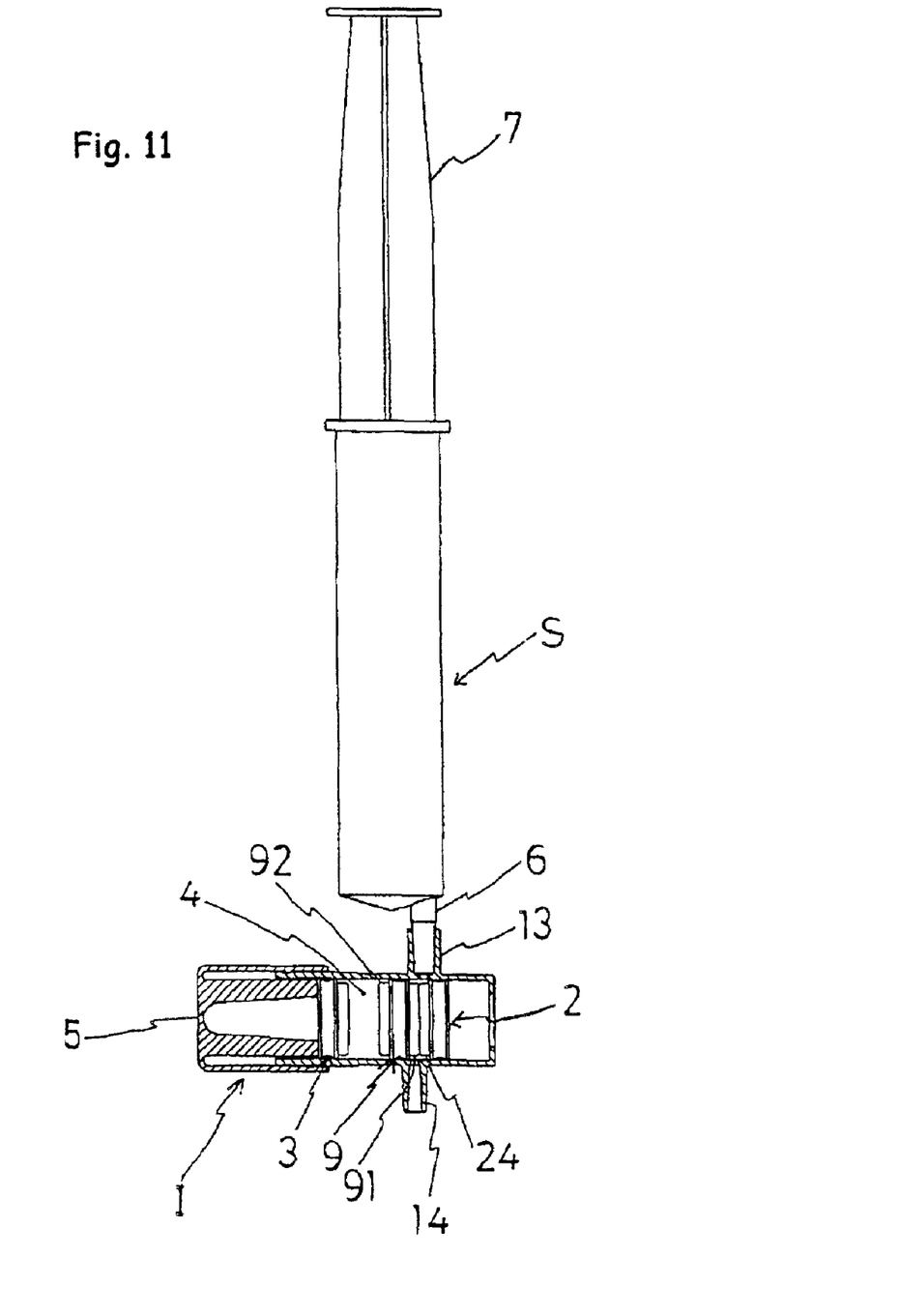
FIGS. 11 through 13 illustrate sequential steps of operation of the injector shown in FIG. 10.
Figure 12:
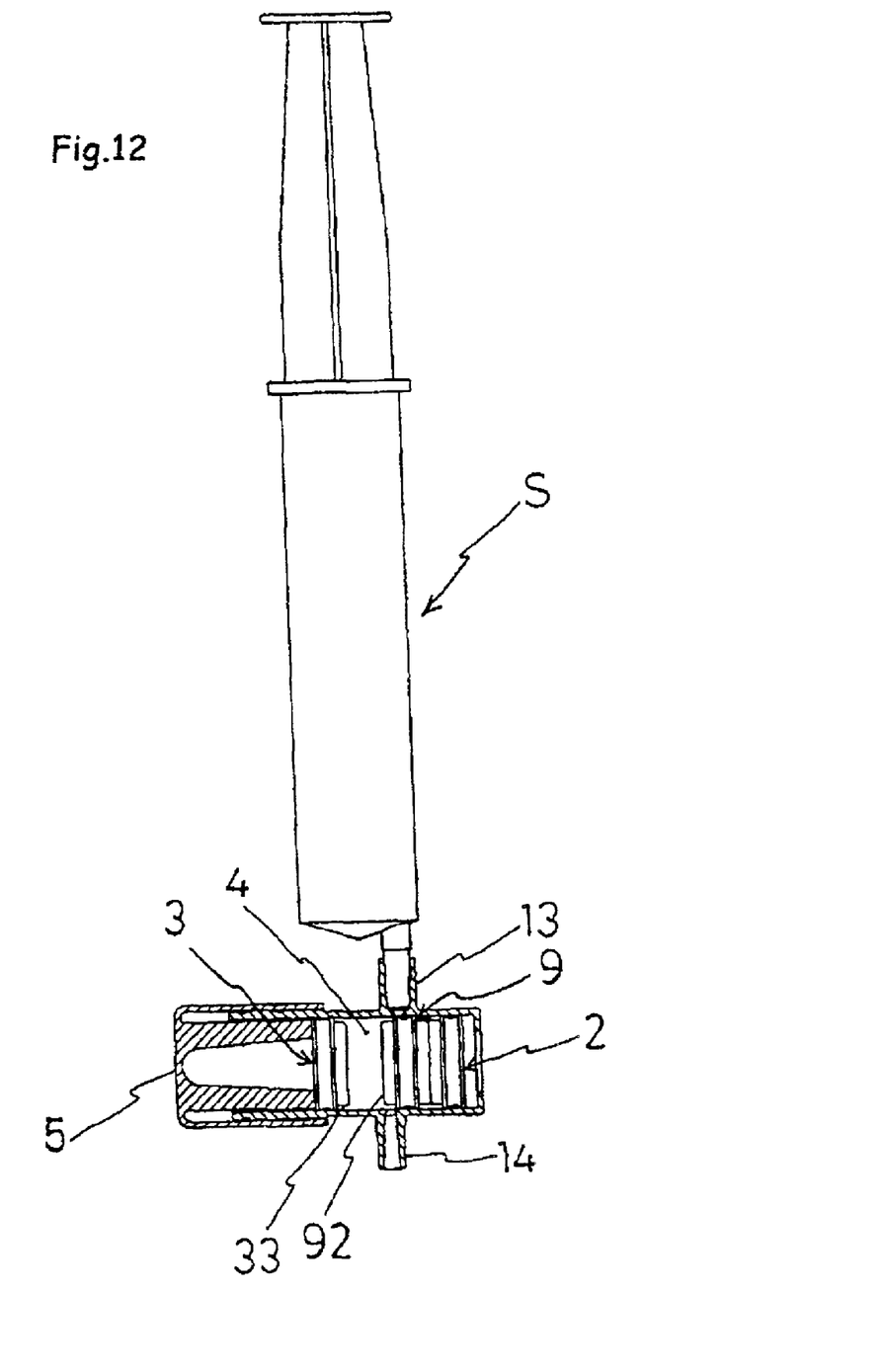
Figure 13:
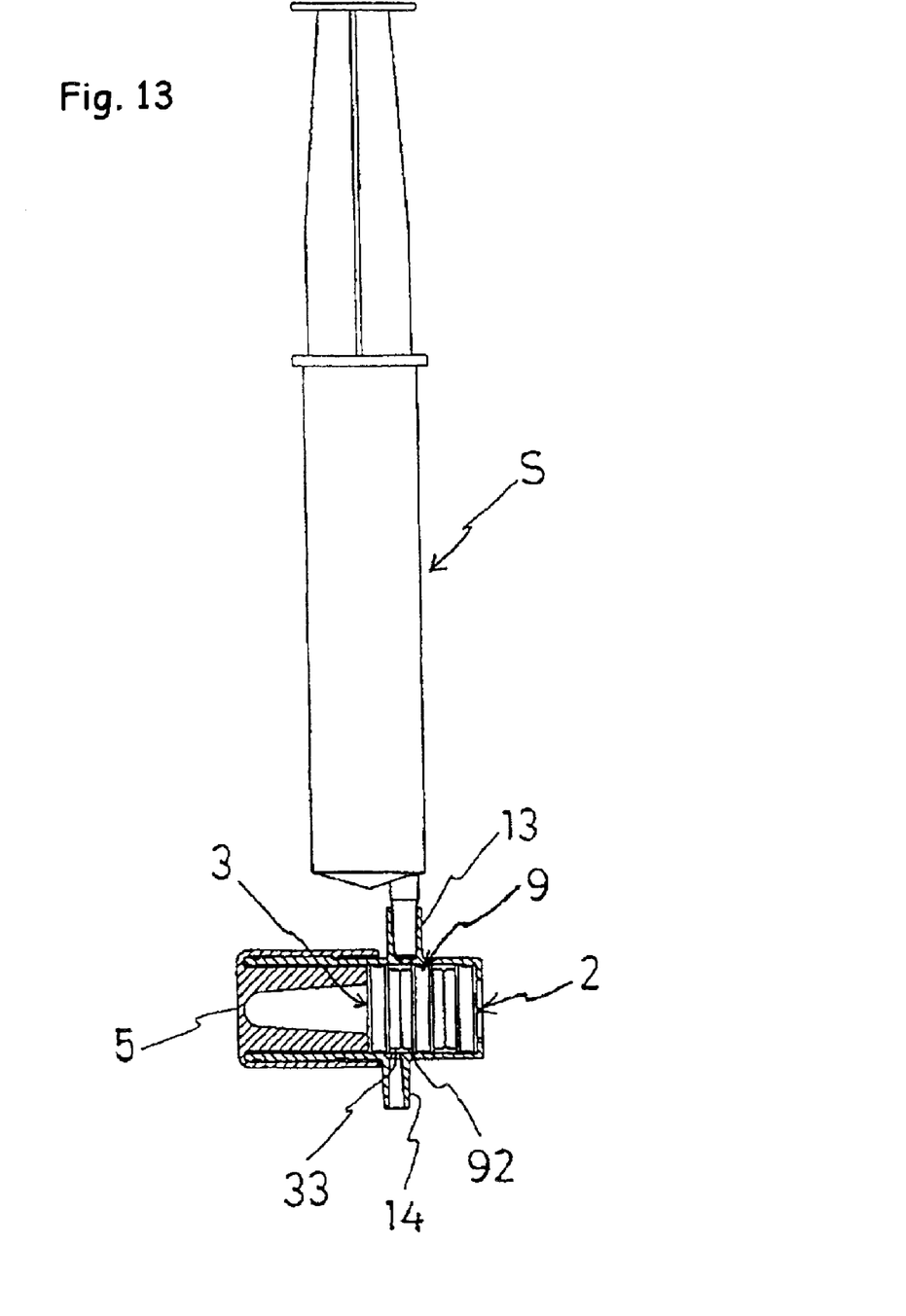

An example of how the medicine injector of FIG. 10 is used will be made with reference to FIGS. 11 to 13 which illustrate a sequence of operation for injecting contrast media into a vein.

Firstly, a liquid medicine injector I with a fluid chamber 4 filled with a dose of contrast media (not illustrated) is prepared and fitted with a needle, e.g., a winged catheter, by fitting it into the fluid outlet 14 thereof. At that time, the first gasket 2 is located at the first position where it allows the fluid inlet 13 to be communicated with the fluid outlet 14 through the gaps formed between the protrusions 24, 91 and the inner wall of the cylindrical body 1. Then, the injector I is fitted with a syringe S containing saline, by fitting a tip 6 of the syringe S in the fluid inlet 13 of the injector I, as illustrated in FIG. 11. By pressing a plunger 7 of the syringe S, the saline in the syringe S is ejected forcefully through the winged catheter via the fluid inlet 13, gaps and outlet 14, so that the whole length of the flow channel for the contrast media is washed with the saline.

After completing the above priming operation, the winged catheter is inserted in a vein of a patient. The plunger 5 of the injector I is then pressed to move the second gasket 3, fluid chamber 4, third gasket 9 and first gasket 2 toward the distal end of the injector I until the first gasket 2 is stopped at the second position where the fluid chamber 4 is communicated with the fluid outlet 14 through the gap between the protrusion 92 and the inner surface of the cylindrical body 1 but prevented from the fluid-communication with the fluid inlet 13, as illustrated in FIG. 12. By further pressing the plunger 5 under such a condition, the contrast media in the fluid chamber 4 is injected through the winged catheter into the vein. As soon as the fluid chamber 4 is emptied, the second gasket 3 is brought into contact with the third gasket 9 and then moved together with the first and third gaskets 2 and 9 toward the distal end 11 of the cylindrical body 1 until the first gasket 2 reaches to the distal end 11 of the cylindrical body 1. At that time, the fluid inlet 13 is communicated with the fluid outlet 14 through the gaps between the cylindrical protrusion 92, 33 and the inner wall of the cylindrical body 1, as illustrated in FIG. 13. By pressing the plunger 7 of the syringe S, the saline is injected into the vein through the fluid inlet 13, gaps between the protrusion 92, 33 and inner wall of the cylindrical body 1, fluid outlet 14 and winged catheter. Thus, the contrast media present in the flow path between the fluid outlet 14 and winged catheter is injected into the vein together with the saline.

As will be understood from the above, since the administration mode can be changed only by simple pushing operation of the plunger, the injector of the present invention is easy to operate. Further, it is possible to administer different medicines sequentially. This is convenient for administration of a small dose of an expensive medicine. After administration of a first medicine, the subsequent second medicine is scarcely mixed with the previous first medicine. Thus, there is no dilution of the subsequent medicine during administration, which in turn makes it possible to perform effective administration. In addition, the expensive medicine remained in route of administration can be injected into the site by injecting the first inexpensive medicine thereafter. This makes it possible to minimize loss of the expensive medicine.

What is claimed is:

1. An injector for liquid medicines comprising:

a cylindrical body having an opening at each end thereof and provided with a fluid inlet and a fluid outlet forming side openings through opposite sides of the cylindrical body, axes of the side openings being substantially perpendicular to a longitudinal axis of the cylindrical body, said inlet and said outlet respectively communicating with a lumen of the cylindrical body, said inlet opening at a position closer to the distal end of the cylindrical body than where the fluid outlet opens; and first and second gaskets fluid-tightly and slidably arranged in the lumen of said cylindrical body and adapted to be moved along an inner wall of said cylindrical body, said first and second gaskets being spaced from one another to form a fluid chamber between them, said fluid chamber being filled with a liquid medicine;

said first gasket being slidable from a first position where the fluid inlet and outlet are communicated with one another, to a distal end of the cylindrical body via a second position where said fluid chamber is prevented from fluid-communication with the fluid inlet but communicating with the fluid outlet to inject the liquid medicine in the fluid chamber through the fluid outlet.

2. The injector according to claim 1, wherein said first gasket has sealing portions adjacent to each end thereof and is provided with a flow path between the sealing portions to allow the fluid inlet of the cylindrical body to communicate with the fluid outlet through the flow path when said first gasket is present at the first position, wherein at least one of the proximal end of first gasket and the distal end of the second gasket is provided with a cylindrical protrusion having an outer diameter smaller than an inner diameter of the cylindrical body so that the first gasket and/or second gasket allows the fluid inlet to communicate with the fluid outlet through an annular gap formed between the cylindrical body and the protrusion when the first gasket is moved to the distal end of cylindrical body.

3. The injector according to claim 2, wherein said flow path is a circumferential groove or channel formed between sealing portions.

4. The injector according to claim 2, wherein said flow path is a through-hole formed between sealing portions and passing through the gasket.

5. The injector according to any claim 2, wherein said cylindrical body is provided at a proximal end thereof with a plunger for pushing the second gasket toward the distal end of the cylindrical body.

\* \* \* \* \*